(12) United States Patent
Moro et al.

(10) Patent No.: US 6,585,997 B2
(45) Date of Patent: Jul. 1, 2003

(54) MUCOADHESIVE ERODIBLE DRUG DELIVERY DEVICE FOR CONTROLLED ADMINISTRATION OF PHARMACEUTICALS AND OTHER ACTIVE COMPOUNDS

(75) Inventors: Daniel G. Moro, Dallas, TX (US); Howard Callahan, North Richland Hills, TX (US); David Nowotnik, Colleyville, TX (US)

(73) Assignee: Access Pharmaceuticals, Inc., Dallas, TX (US)

( * ) Notice: Subject to any disclaimer, the term of this patent is extended or adjusted under 35 U.S.C. 154(b) by 7 days.

(21) Appl. No.: 09/931,319

(22) Filed: Aug. 16, 2001

(65) Prior Publication Data

US 2003/0044446 A1 Mar. 6, 2003

(51) Int. Cl.[7] .............................. A61F 2/02; A61L 15/16
(52) U.S. Cl. ...................... 424/434; 424/435; 424/448; 424/449
(58) Field of Search ................................ 424/434, 435, 424/448, 449

(56) References Cited

U.S. PATENT DOCUMENTS

| | | | |
|---|---|---|---|
| 3,948,254 A | 4/1976 | Zaffaroni | 128/833 |
| 3,993,072 A | 11/1976 | Zaffaroni | 424/430 |
| 3,996,934 A | 12/1976 | Zaffaroni | |
| 4,226,848 A | 10/1980 | Nagai et al. | 424/19 |
| 4,250,163 A | 2/1981 | Nagai et al. | 424/14 |
| 4,286,592 A | 9/1981 | Chandrasekaran | 128/260 |
| 4,292,299 A | 9/1981 | Suzuki et al. | 424/16 |
| 4,517,173 A | 5/1985 | Kizawa et al. | 424/16 |
| 4,518,721 A | 5/1985 | Dhabhar et al. | 523/120 |
| 4,552,751 A | 11/1985 | Inaba et al. | 424/19 |
| 4,572,832 A | 2/1986 | Kigasawa et al. | 424/19 |
| 4,615,697 A | 10/1986 | Robinson | 424/428 |
| 4,713,243 A | 12/1987 | Schiraldi et al. | 242/151 |
| 4,715,369 A | 12/1987 | Suzuki et al. | 128/156 |
| 4,894,232 A | 1/1990 | Reul et al. | 424/439 |
| 4,900,554 A | 2/1990 | Yanagibashi et al. | 424/448 |
| 4,915,948 A | 4/1990 | Gallopo et al. | 424/435 |
| 5,047,244 A | 9/1991 | Sanvordeker et al. | 424/435 |
| 5,081,157 A | 1/1992 | Pomerantz | 514/781 |
| 5,081,158 A | 1/1992 | Pomerantz | |
| 5,137,729 A | 8/1992 | Kuroya et al. | 424/435 |
| 5,139,023 A | 8/1992 | Stanley et al. | 600/368 |
| 5,192,802 A | 3/1993 | Rencher | 514/781 |
| 5,291,887 A | 3/1994 | Stanley et al. | 600/573 |
| 5,298,258 A | 3/1994 | Akemi et al. | 424/484 |
| 5,314,915 A | 5/1994 | Rencher | 514/535 |
| 5,458,879 A | 10/1995 | Singh et al. | 424/400 |
| 5,462,749 A | 10/1995 | Rencher | |
| 5,474,768 A | 12/1995 | Robinson | |
| 5,543,150 A | 8/1996 | Bologna et al. | |
| 5,578,315 A | 11/1996 | Chien et al. | 424/435 |
| 5,624,677 A | 4/1997 | El-Rashidy et al. | 424/435 |
| 5,667,492 A | 9/1997 | Bologna et al. | |

(List continued on next page.)

FOREIGN PATENT DOCUMENTS

| | | |
|---|---|---|
| EP | 0765664 A | 4/1997 |
| EP | 0765664 A1 | 4/1997 |
| GB | 1593097 A | 7/1981 |
| GB | 1593097 | 7/1981 |
| JP | 59186913 | 10/1984 |
| US | 6166044 A | 12/2000 |
| WO | 9609829 | 4/1996 |
| WO | 9609829 A | 4/1996 |
| WO | 9801112 | 1/1998 |
| WO | 9801112 A | 1/1998 |
| WO | WO 98/17251 | 4/1998 |
| WO | WO 99/55312 | 11/1999 |
| WO | 9963986 A | 12/1999 |
| WO | WO 00/42959 | 7/2000 |
| WO | 0050078 | 8/2000 |
| WO | 02/09637 A2 | 2/2002 |
| WO | 0209637 A2 | 2/2002 |

OTHER PUBLICATIONS

Dr. Marcello Innocenti, Clinical Evaluation of Gelcair Concentrtated Oral Gel, a new option for treating painful oral conditions, pp. 1–14, Milan, Italy.

PDR 21 Edition 2000, Physicians Desks Reference for Nonprescription Drugs and Dietary Supplements, pp. 640 and 787.

Dr. Heddie Sedano, Oral Complications During Cancer Treatment, Jun. 13, 2002, pp. 1–5.

Jelka Korbar–Smid et al, An Oxtetracycline Formulation to be Applied at the Oral Mucosa, Aug. 5, 1975, pp. 271–276, University of Ljubljana.

Dixon J, Search Conducted on hyaluronic Acid and Mucositis, May 29, 2002, pp. all, US Kaken Seiyaku KK, Abstract, JP 59186913, Apr. 4, 1983.

Tsumura & Co, Abstract JP 8291083, Apr. 17, 1995.

Jian–Hwa, et al Bioadhesive Polymer Buccal Patches for Buprenorphine Controlled Delivery: Solubility; 1995; 2013–1019; Drug Development and Industrial Pharmacy.

(List continued on next page.)

Primary Examiner—Carlos A. Azpuru
(74) Attorney, Agent, or Firm—Jackson Walker, LLP

(57) ABSTRACT

The present invention relates to a layered pharmaceutical delivery device for the administration of pharmaceuticals or other active compounds to mucosal surfaces. The device may also be used by itself without the incorporation of a therapeutic. The device of the present invention consists of a water-soluble adhesive layer, a non-adhesive, bioerodable backing layer and one or more pharmaceuticals if desired in either or both layers. Upon application, the device adheres to the mucosal surface, providing protection to the treatment site and localized drug delivery. The "Residence Time", the length of time the device remains on the mucosal surface before complete erosion, can be easily regulated by modifications of the backing layer.

51 Claims, No Drawings

U.S. PATENT DOCUMENTS

| | | | |
|---|---|---|---|
| 5,750,134 A | 5/1998 | Scholz et al. | 424/434 |
| 5,750,136 A | 5/1998 | Scholz et al. | 424/448 |
| 5,766,620 A | 6/1998 | Heiber et al. | 424/436 |
| 5,780,045 A | 7/1998 | McQuinn et al. | 424/435 |
| 5,783,207 A | 7/1998 | Stanley et al. | 424/440 |
| 5,800,832 A | 9/1998 | Tapolsky et al. | 424/449 |
| 5,827,525 A | 10/1998 | Liao et al. | 424/435 |
| 5,849,322 A | 12/1998 | Ebert et al. | 424/435 |
| 5,855,908 A | 1/1999 | Stanley et al. | 424/440 |
| 5,861,174 A | 1/1999 | Stratton et al. | 424/484 |
| 5,863,555 A | 1/1999 | Heiber et al. | 424/435 |
| 5,869,082 A | 2/1999 | Dugger, III | 424/435 |
| 5,888,534 A | 3/1999 | El-Rashidy et al. | 424/435 |
| 5,900,230 A | 5/1999 | Cutler | |
| 5,908,637 A | 6/1999 | Benes et al. | 424/464 |
| 5,955,097 A | 9/1999 | Tapolsky et al. | 424/434 |
| 5,955,098 A | 9/1999 | Dugger, III | 424/435 |
| 5,968,500 A | 10/1999 | Robinson | |
| 5,981,499 A | 11/1999 | Hau | 514/29 |
| 6,017,521 A | 1/2000 | Robinson et al. | |
| 6,071,959 A * | 6/2000 | Rhodes et al. | |
| 6,103,226 A * | 8/2000 | Kang et al. | |
| 6,103,266 A | 8/2000 | Tapolsky et al. | 424/484 |
| 6,110,486 A | 8/2000 | Dugger, III | 424/435 |
| 6,117,446 A | 9/2000 | Place | 424/435 |
| 6,159,498 A | 12/2000 | Tapolsky et al. | 424/449 |
| 6,166,044 A | 12/2000 | Sandborn et al. | |

OTHER PUBLICATIONS

Hussain, et al Improved Buccal Delivery of Opioid Analgesics and Antagonist with Bitterness Prodrugs; 1998; 615–618; Pharmaceutical Research.

Badawy, et al. Bioavailability of danazol–hydroxypropyl–Beta–cyclodextrin comples by different routes of administration; 1996; 137–143; International Journal of Pharmaceutics.

Kutcher, et al Evaluation of a bioadhesive device for the management of aphthous ulcers; 1998–2001; 1–13; Advances in Dental Products.

Hoogstraate, et al Buccal delivery of fluorescein isothiocyanate–dextran 4400 and peptide drug buserelin with glycodeoxycholate as adsorption enhancer in pigs; 1996; 77–84; Journal of Controlled Release.

Li, et al Evaluation of a Mucoadhesive Buccal Patch for Delivery of Peptides; In Vitro Screening of Bioadhesion; 1998; 919–926; drug Development and Industrial Pharmacy.

Nielsen, et al Bioadhesive drug delivery systems I. Characterisation of mucoadhesive properties of systems based on glyceryl mono–oleate and glyceryl monolinoleate; 1998; 231–239; European Journal of Pharmaceutical Sciences.

Warren The Synthesis and In Vitro Characterization of the Mucoadhesion and Swelling of Poly(Acrylic Acid) Hydrogels; 1998; 199–208; Pharmaceutical Development and Technology.

Tamburic, et al The Effects of Ageing on the Pheological, Dielectric and Mucoadhesive Properties of Poly(Acrylic Acid) Gel System; 1996; 279–283; Pharmaceutical Research.

Pather, et al Enhanced Buccal Delivery of Fentanyl Using The Oravescent™ Drug Delivery System; Cima Labs Inc.

Kim, et al Buccal Delivey of Butorphanol Tartrate By Using Mucoadhesive P(AA–co–PEGMM) Film; ; 361–763; College of Pharmacy, Chungbuk National University, Cheongju, Korean.

Kremer, et al Permeabilizing Effect of Different Chitosans on Drug Delivery Across Buccal Mucosa; Dows Institute For Dental Research; University of Iowa, Iowa City, Iowa.

Ali, et al In Vivo Evaluation of Bioadhesive Erodible Disk of Cetylpyrodinium Chloride and Comparison of Its Effect With Mouthwash In Oro–Dental Infections; Department of Pharmaceutics, Faculty of Pharmacy.

Kalra, et al Bilayered Buccoadhesive Wafers of An Antihypertensive Agent: Formulation and Evaluation; Department of Pharmaceutics.

Gandhi, et al Oral Mucosal Drug Delivery System of Trimetazidine Dihydrochloride; Pharmaceutical Division, University Department of Chemical Technology.

* cited by examiner

MUCOADHESIVE ERODIBLE DRUG DELIVERY DEVICE FOR CONTROLLED ADMINISTRATION OF PHARMACEUTICALS AND OTHER ACTIVE COMPOUNDS

FIELD OF THE INVENTION

The present invention relates to a bioerodable pharmaceutical carrier device that adheres to mucosal surfaces for the localized, controlled delivery of pharmaceuticals or other active compounds and/or the protection of the underlying treatment site.

BACKGROUND OF THE INVENTION

The localized treatment of body tissues, diseases and wounds requires that a particular pharmaceutical be administered and maintained at the treatment site for a therapeutically effective period of time. The topical treatment of wet, mucosal surfaces has been problematic, since natural bodily fluids can rapidly wash away a topically applied active compound before the appropriate therapeutic action to the underlying surface can occur. In the mouth, saliva, the natural replacement of the mucosal tissue, and the actions of eating, speaking and drinking are just some of the problems that have limited the usefulness of pharmaceutical carrier devices.

Gels, pastes, tablets and films have been developed as bioadhesive carriers and are well known in the art. These types of products, however, do not exhibit all of the major characteristics required for an efficient and commercially acceptable pharmaceutical delivery device for mucosal treatment. The important characteristics include, water erodability, ease of handling and application to the treatment site, comfort with minimal foreign body sensation, rapid adhesion, prolonged residence time for the protection of the treatment site and/or the delivery of a pharmaceutical or other active compound, and ease of removal from the underlying mucosal surface by natural erosion or dissolution of the delivery device at the treatment site.

Bioadhesive gels used especially in the oral mucosal cavity are known in the art. For example, U.S. Pat. No. 5,192,802 describes a bioadhesive teething gel composed of a mixture of sodium carboxymethyl cellulose and xanthan gum. This gel composition may have potential use in the treatment of canker sores, fever blisters and hemorrhoids. However, these types of gel systems have limited residence times, since bodily fluids such as saliva will quickly wash gels away from the treatment site. Other bioadhesive gels described in U.S. Pat. Nos. 5,314,915; 5,298,258 and 5,642,749 use an aqueous or oily medium and different types of bioadhesive and gelling materials, but still suffer from the inherent limitation of all gel products. Another type of bioadhesive products known in the art is denture adhesive pastes. These products, however, were developed primarily for their adhesive properties only, and not to protect tissue or deliver pharmaceuticals to the underlying mucosal surface. However, active compounds such as local anesthetics may be formulated with the paste for the relief of sore gums. Denture adhesive pastes are described in U.S. Pat. Nos. 4,894,232 and 4,5518,721. In the '721 patent, the combination of sodium carboxymethyl cellulose and polyethylene oxide in polyethylene glycol is used to provide a bioadhesive composition. Mucoadhesive pastes have also been used as protective films and drug delivery systems. Orabase®-B, a commercialized paste product that has both film forming and adhesive properties, is used for the relief of mouth sores. This product does provide numbing of the treatment site, but the residence time is small due to the quick dissolution by saliva. This product contains guar gum, sodium carboxymethyl cellulose, tragacanth gum and pectin.

Bioadhesive tablets are described in U.S. Pat. No. 4,915,948. A xanthan gum or a pectin in combination with an adhesion enhancing material such as polyol is the water-soluble bioadhesive used in this device. Although the residence time is greatly enhanced, these tablets are not user friendly, especially when used in the oral cavity, due to their unpleasant feeling, solidity, bulkiness and slow dissolution time. Also, solid devices cannot readily adhere to curved surfaces, especially crevices within the oral cavity. Bioadhesive tablets described in U.S. Pat. Nos. 4,226,848; 4,292,299, and 4,250,163 are single or bilayer devices having an average thickness of 0.2 to 2.5 mm. These devices are less bulky, but have limited residence times. They are composed of a non-adhesive material such as cellulose ether, a bioadhesive ingredient such as polyacrylic acid, sodium carboxymethyl cellulose, or polyvinylpyrrolidone, and a binder for tableting purposes. The cellulose derivatives used in these devices may or may not be water-soluble. The bilayer devices described in the '299 patent contain methyl cellulose, hydroxypropyl cellulose and hydroxypropylmethyl cellulose. Bandages and bioadhesive laminated films are also known in the art. The films as described in U.S. Pat. Nos. 3,996,934 and 4,286,592 are thinner, more flexible and therefore elicit a decreased foreign body sensation. The laminated films are usually composed of an adhesive layer, a reservoir layer and a backing layer and are designed to deliver drugs through the skin or mucosa. These films are typically not water soluble, thus they are not dissolved or washed away by bodily fluids and must be removed after the prescribed treatment time.

Film delivery systems for use on mucosal surfaces are also known in the art. These types of systems, which are water-insoluble and usually in the form of a laminated, extruded or composite film, are described in U.S. Pat. Nos. 4,517,173; 4,572,832; 4,713,243; 4,900,554 and 5,137,729. The '173 patent relates to a membrane-adhering film composed of at least three layers, including a layer containing a pharmaceutical, a layer with limited water solubility, and an intermediate layer. The pharmaceutical layer contains a drug and a cellulose derivative selected from hydroxypropyl cellulose, methyl cellulose, and hydroxypropylmethyl cellulose. The layer having limited water solubility consists of a combination of one or more cellulose derivatives and a hydrophobic fatty acid, and the intermediate layer is made of cellulose derivatives. The '832 patent describes a\soft film for buccal delivery. The film is composed of a water soluble protein, a polyol, and a polyhydric alcohol such as cellulose and polysaccharides and coloring and flavoring agents. The '243 patent relates to a single or multi-layered bioadhesive thin film made from 40–95% water soluble hydroxypropyl cellulose, 5–0% water-insoluble ethylene oxide, 0–10% water-insoluble ethyl cellulose, propyl cellulose, polyethylene or polypropylene and a medicament. These films are three-layered laminates and are composed of a bioadhesive layer, a reservoir layer, and a non water-soluble outer protective layer. The '729 patent teaches a soft, adhesive film for use on oral mucosa. The film is comprised of a mixture of vinyl acetate non water-soluble homopolymer, an acrylic acid polymer, a cellulose derivative and a systemic drug.

In the '554 patent, the device is designed for use in the oral cavity and is composed of an adhesive layer including a mixture of an acrylic acid polymer, a water-insoluble cellulose derivative, a water-insoluble or sparingly soluble backing layer, and a pharmaceutical. The adhesive layer contains the active ingredient and upon application to the treatment site, the drug is delivered to the underlying mucosal surface. This patent also teaches that all three of the aforementioned components are required to attain an appropriate adhesive device suitable for mucosal treatment and drug delivery.

Finally, bioerodable films for the delivery of pharmaceutical compounds are also known in the art. U.S. Pat. Nos. 5,800,832 and 6,159,498 describe a bioerodable, water soluble pharmaceutical device to treat mucosal surfaces. These bilayer devices are composed of an adhesive layer and a non-adhesive backing layer, and the pharmaceutical may be contained in either or both layers.

The composition of the adhesive layer comprises polyacrylic acid, sodium carboxymethyl cellulose, and polyvinyl pyrrolidone, alone or in combination thereof. In addition to these mucoadhesive polymers, film forming polymers such as hydroxyethyl cellulose and hydroxypropyl cellulose are present. This layer can also contain a pharmaceutical compound. The backing layer of these devices comprises only film-forming polymers, such as hydroxyethyl cellulose, hydroxypropyl cellulose and hydroxypropylmethyl cellulose. These polymers are known to exhibit low bioadhesion and are approved for use in a variety of pharmaceutical applications. The residence time is claimed to be regulated by only variations of the backing layer. To increase the residence time, the components of the backing layer can be crosslinked with glyoxal solution, rendering the polymers less water soluble, and therefore, slower to dissolve, while being exposed to bodily fluids like saliva. A second approach is to change the composition of the backing layer by using a mixture of different and higher molecular weight polymers from the same family of hydroxyethyl and hydroxypropyl celluloses. These alterations to the backing layer are easy to accomplish. However, they do not provide a consistent, controllable and reproducible residence time for the final device. In addition, in order to produce this device, it is required to cast the mucoadhesive layer and/or backing layer onto a hard and non-porous surface. Then, each layer is dried yielding a laminated film. The casting surface therefore becomes an integral part of the device or must be carefully removed from the laminated film prior to cutting to the desired shape and subsequent packaging. The associated manufacturing processes to produce such a device are complicated and therefore are not commercially viable or cost effective.

SUMMARY OF THE INVENTION

The present invention relates to a novel, cost-effective, commercially viable, water-erodible, pharmaceutical carrier device. The device is applied to mucosal surfaces and provides protection of the application site while delivering pharmaceuticals to treat specific diseases or disorders. The device causes minimum discomfort, is easy to use and provides an effective residence time that can be tailored to deliver therapeutics over different time intervals. In one embodiment, the device comprises a mucoadhesive multi-layered film disc that is water-soluble and bioerodable. In another embodiment, the pharmaceutical delivery device comprises a multi-layered film having an adhesive layer and a coated backing layer containing a pharmaceutical or other active compound in either or both layers. The film may be cut or fabricated into any desired shape, such as a disc, square, oval, parallelepiped, etc., that provides convenience for use in application and/or treatment. The adhesive layer of the device is water soluble and the backing layer is bioerodible. The adhesive layer comprises a film-forming polymer such as hydroxyethyl cellulose, hydroxypropyl cellulose, hydroxypropylmethyl cellulose, or hydroxyethylmethyl cellulose, alone or in combination, and a bioadhesive polymer such as polyacrylic acid, polyvinyl pyrrolidone, or sodium carboxymethyl cellulose, alone or in combination. The non-adhesive backing layer is a precast film alone or in combination with other layers. The precast film is comprised of hydroxyethyl cellulose, hydroxypropyl cellulose, hydroxyethylmethyl cellulose, hydroxypropylmethyl cellulose, polyvinyl alcohol, polyethylene glycol, polyethylene oxide, ethylene oxide-propylene oxide co-polymers, or other water soluble film-forming polymer, alone or in combination thereof. The precast film may also include plasticizers or other excipients required to enhance the film forming properties of the polymer. The non-adhesive backing layer is further modified to render it water erodible instead of water soluble. For definition purpose, water erodible means a material or substance that does not dissolve in in water or bodily fluids in total, however will disintegrate and completely break apart upon exposure to water or bodily fluids. This is accomplished by coating the backing layer film with a more hydrophobic polymer selected from a group of Eudragit® and/or ethyl cellulose and methyl cellulose polymers that are approved by the FDA for use in pharmaceutical applications. Other hydrophobic polymers known to those skilled in the art may also be used. The type and amount of hydrophobic polymer used will provide a wide and controlled range of Residence Times for the layered disk device. In addition, the modified, precast backing layer eliminates the need to use a rigid support material such as a polyethylene film or other non-porous material as the casting surface on which both the adhesive layer and backing layer are produced. This casting surface is no longer an integral component of the layered device, which from a safety and production point of view, is extremely desirable.

An important aspect of the present invention concerns a mucoadhesive erodible multi layered device comprising first water soluable adhesive layer to be placed in contact with a mucosal surface and second water erodible non-adhesive backing layer that controls residence time of the device. Residence time, the time for which device in placed on the target mucosal surface will remain substantially intact). The first layer comprises at least one water soluble film forming element in combination with at least one mucoadhesive polymer. The second water erodible non adhesive backing layer comprises a precast film containing at least one of hydroxypropyl methylcellulose, hydroxyethyl cellulose, hydroxypropyl cellulose, polyvinyl alcohol, polyethylene glycol, polyethylene oxide, and ethylene oxide-propylene oxide co-polymer. This layer is coated with at least one hydrophobic polymer alone or in combination with at least one hydrophilic polymer, such that the layer is bioerodible.

This device may be used by itself or may be used with an incorporated pharmaceutical agent. This device may be used for the protection of a mucosal site and/or the administraton of a pharmaceutical agent locally, regionally or systemically. In a preferred embodiment, the first water-soluble adhesive layer comprises at least one water-soluble film-forming polymer selected from the group consisting of hydroxyethyl cellulose, hydroxypropyl cellulose, hydroxypropyl methylcellulose, and hydroxyethyl methylcellulose, in combination with at least one mucoadhesive polymer selected from the group consisting of polyacrylic acid, polyvinyl pyrrolidone, and sodium carboxymethyl cellulose. The second water erodible non-adhesive backing layer may act as a casing and support surface on which the adhesive layer is prepared. This second layer preferably comprises a premade film of hydroxypropyl methylcullulose in combination with a coating consisting of at least one hydrophobic polymer selected from the family of Eudragit polymers, ethyl cellulose and methylcellulose alone or in combination with at least hydrophilic polymer selected from the group consisting of polyvinyl pyrrolidone, hydroxypropylmethylcellulose, hydroxyethylmethylcellulose, hydroxypropylcellulose and polyvinylalcohol.

In certain preferred embodiments the mucoadhesive bioerodible multilayered device of the present invention has a second water erodible non-adhesive backing layer that comprises a pre-made film of hydroxypropyl methylcullulose and a coating of a hydrophobic and hydrophilic polymer mixture at a ratio of 0.5:1 to 18:1. A more preferred ratio is 1:0 to 10:1.

In an important embodiment, the non-adhesive backing layer of the device of the present invention comprises a precast film of hydroxypropyl methylcellulose with a coating mixture of hydrophobic and hydrophilic polymers at a ratio of 1:0 to 10:1. This coating contains at least one of propylene glycol, polyethylene glycol or glycerine as a plasticizer to improve flexibility. A preferred non-adhesive backing layer of the device of the present invention comprises a premade film of hydroxypropyl methylcellulose and a coating mixture of hydrophobic and hydrophilic polymers at a ratio of 1:0 to 10:1. A preferred coating mixture contains at least one of hyaluronic acid and an alpha hydroxyl acid as a humectant to improve softness or feel. A preferred humectant is glycolic acid.

In one particularly preferred embodiment, the mucoadhesive erodible multi layered device of the present invention has an non-adhesive backing layer that comprises a precast film of hydroxypopyl methylcellulose and a coating mixture of hydrophobic and hydrophilic polymers at a ratio of 1:0 to 10:1. A preferred coating mixture contains titanium dioxide, zinc oxide or zirconium silicate as an opacifier and one or less FD&C Red, Yellow, Green or Blue as a coloring agent to help distinguish the backing layer from the mucoadhesive layer. In one embodiment, the backing layer of the present device comprises a premade film of hydroxypropyl methylcellulose, a coating comprising a mixture of hydrophobic and hydrophilic polymers at a ratio of 1:0 to 10:1, a plasticizer and a coloring agent or an opacifier whose combined total is less than about 4% by weight of the device.

In a very important embodiment of the present invention, the mucoadhesive, erodible multi-layered device further comprises at least one pharmaceutical agent incorporated within said first or second layer. The pharmaceutical agent is defined wherein any agent that has desirable prophylatic or curative effects. Pharmaceutical agents may be incorporated within the first or second layers of the device of the present invention. These layers may each independently comprise flavoring agent to mask the taste of any pharmecutical agent or simply to improve patient compliance.

One class of pharmaceutical agents are anti-allergic agents. Anti-allergic agents may be, e.g., amlexanox, astemizole, azelastinep, emirolast, alopatadine, cromolyn, fenpiprane, repirinast, tranilast, or traxanox.

One pharmaceutical agent that may be a component of the device of the present invention is an anti-inflammatory analgesic agent. Such anti-inflammatory analgesic agents may be, e.g., acetaminophen, methyl salicylate, monoglycol salicylate, aspirin, mefenamic acid, flufenamic acid, indomethacin, diclofenac, aldlofenac, diclofenac sodium, ibuprofen, ketoprofen, naproxen, pranoprofen, fenoprofen, sulindac, fenclofenac, clidanac, flubiprofen, fentiazac, bufexarnac, piroxicam, phenylbutazone, oxyphenbutazone, clofezone, pentazocine, mepirizole, or tiaramide hydrochloride. In some cases the pharmaceutical agent of the present invention may be an antianginal agent. Such antianginal agents may be nifedipine, atenolol, bepridil, carazolol, or epanolol.

Steroidal anti-inflammatory agents may sometimes the pharmaceutical agents of the present invention. Steroidal anti-inflammatory agents may be, e.g., hydrocortisone, predonisolone, dexamethasone, triamcinolone acetonide, fluocinolone acetonide, hydrocortisone acetate, predonisolone acetate, methylpredonisolone, dexamethasone acetate, betamethasone, betamethasone valerate, flutetasone, fluormetholone, or orbeclomethasone dipropionate.

Another usable class of pharmaceutical agents are antihistamines. Such antihistamines may be, e.g., diphenhydramine hydrochloride, chlorpheniramine maleate, isothipendyl hydrochloride, tripelennamine hydrochloride, promethazine hydrochloride, or methdilazine hydrochloride.

The pharmaceutical agent of the present invention may be a local anesthetic, such as, e.g., dibucaine hydrochloride, dibucaine, lidocaine ydrochloride, lidocaine, benzocaine, p-buthylaminobenzoic acid, 2-(di-ethylamino) ethyl ester hydrochloride, procaine hydrochloride, tetracaine, tetracaine hydrochloride, chloroprocaine hydrochloride, oxyprocaine hydrochloride, mepivacaine, cocaine hydrochloride, piperocaine hydrochloride, dyclonine, or dyclonine hydrochloride.

When the preferred pharmaceutical agent is a bactericide or disinfectant, it may, e.g., be thimerosal, phenol, thymol, benzalkonium chloride, chlorhexidine, povidone iodine, cetylpyridinium chloride, eugenol, trimethylanmmonium bromide, benzoic acid or sodium benzoate.

When the pharmaceutical agent of the present invention is a vasoconstrictor, it may be, e.g., naphazoline nitrate, tetrahydrozoline hydrochloride, oxymetazoline hydrochloride, phenylephrine hydrochloride, or tramazolinehydrochloride.

When the pharmaceutical agent incorporated in the device of the present invention is a hemostatic agent, preferably is, e.g., thrombin, phytonadione, protamine sulfate, aminocaproic acid, tranexamic acid, carbazochrome, carbaxochrome sodium sulfate, rutin, or hesperidin.

If the pharmaceutical agent in the device of the present invention is a chemotherapeutic agent, it may be, e.g., sulfamine, sulfathiazole, sulfadiazine, homosulfamine, sulfisoxazole, sulfisomidine, sulfamethizole, nitrofurazone, taxanes, platinum compound, topoisomerase 1 inhibitor, or anthracycline.

When the pharmaceutical agent incorporated in the device of the present invention is an antibiotic it may be, for example, penicillin, meticillin,oxacillin, cefalotin, cefalordin, erythromycin, lincomycin, tetracycline, chlortetracycline, oxytetracycline, chloramphenicol, kanamycin, streptomycin, gentamicin, bacitracin, cycloserine, or clindamycin.

The pharmaceutical agent of the present invention when incorporated into a device as described herein may be a keratolytic agent. Such a keratolytic agent may be, e.g., alicylic acid, podophyllum resin, podolifox, or cantharidin.

When the pharmaceutical agent incorporated into the device of the present invention is a cauterizing agent, it may be chloroacetic acid or silver nitrate.

The pharmaceutical agent incorporated in a device of the present invention may also be a hormone. Such a hormone may be, e.g., estrone, estradiol, testosterone, equilin, or human growth hormone.

This pharmaceutical agent that may be incorporated in a device of the present invention may also be a growth hormone inhibitor. Preferred growth hormone inhibitors include octreotide or somatostatin.

If the incorporated pharmaceutical agent is an analgesic narcotic it may be, for example, fentanyl, buprenorphine, codeine sulfate, levophanol, or morphine hydrochloride.

If this pharmaceutical agent is an antiviral agent, it may be, for example, protease inhibitor, thymidine kinase inhibitor, sugar or glycoprotein synthesis inhibitor, structural protein synthesis inhibitor, attachment and adsorption inhibitor, or nucleoside analogue.

Such a nucleoside analogue may be acyclovir, penciclovir, valacyclovir, or ganciclovir.

In the most preferred embodiments in the present invention, when pharmaceutical agents are added, they are between 0.001 percent and about 30.00 percent by weight of the device. More preferably, the pharmaceutical agent is between about 0.005 and about 20 percent by weight of the device.

DETAILED DESCRIPTION OF THE INVENTION

In the present invention, a unique bioerodible miltilayered device that adheres to mucosal surfaces is provided. The present invention is most applicable to the treatment of body tissues, diseases, or wounds that may have moist surfaces and that are susceptible to bodily fluids, such as the mouth, vagina, anus, or other types of mucosal surfaces. Pharmaceuticals or other active compounds can be incorporated in the device, and upon application and adherence to the specific mucosal site, protection of the underlying tissue results.

Concomitantly, pharmaceuticals are delivered to the treatment site, the surrounding tissues and other bodily fluids for a prolonged period of time. The device provides an appropriate, controlled residence time for effective drug delivery at the treatment site. The residence time is easily tailored to provide a range from minutes to hours, dependent upon the type of drug used and therapeutic indication. In one embodiment, the pharmaceutical delivery device comprises a layered film disc having a water soluble adhesive layer and a water erodible backing layer, having a pharmaceutical in either or both layers.

The present invention offers advantages with respect to increased residence time over bioadhesive gels and pastes known in the art. Paste and gel products such as Orajel, Orabase, and Kanka have short residence times in the order of minutes. This is a result of limited or poor adhesion. Upon application of a gel product to the mucosal surface, the mucoadhesive components do not instantaneously penetrate the lipophilic surface of the mucosa. Instead, these hydrophilic components quickly mix with saliva or other bodily fluids and therefore are removed from the application site resulting in a minimal residence time. A similar mechanism of action can be expected to occur with paste products, however to a slightly lesser extent. This is due to the higher viscosity and greater hydrophobicity of the paste causing a slower erosion process to occur. The film of the present invention provides for immediate adhesion to the mucosal surface due to the combination of mucoadhesive polymers within water-soluble film-forming polymers, and its thin, flexible solid form. A solid device will dissolve or erode more slowly than a gel or paste device due to dissolution kinetics.

Bioadhesive tablets known in the art also have serious limitations, primarily due to their bulkiness and rigidity causing an unpleasant sensation and discomfort after application to the oral cavity. These tablets provide effective residence times, but because they are an order of magnitude larger than the device in the present invention, the preferred application site is on the upper gingival or sublingual area. This site is suitable for systemic delivery of an active compound, but may not be satisfactory for localized, unidirectional delivery. The device of the present invention offers both local and systemic delivery with an effective and controlled residence time and minimal discomfort and ease of application as a result of its thinner, more flexible configuration.

Finally, film systems known in the art that are used to deliver pharmaceuticals also have other limitations. These films, unlike the pharmaceutical device of the present invention, are occlusive and water insoluble and are fabricated to be removed after treatment of a mucosal surface. Removal of a non-erodible device may cause some damage to the mucosa, or may damage healing mucosa when the device is used to cover a lesion. The pharmaceutical device of the present invention is designed to be water erodible, and therefore does not require removal. Once applied to a mucosal surface, water absorption softens the device, and over time, the device slowly erodes away delivering a specific pharmaceutical to the treatment site.

In one embodiment, the present invention is composed of a multi-layered film having an adhesive layer, a precast non-adhesive backing layer, and a hydrophobic coating layer. The hydrophobic coating layer renders the backing layer water-erodible instead of water soluble, allows the precast backing layer to be the support layer and provides a wide range of predictable and controlled residence times. The adhesive layer is water soluble and the backing layer is water erodible. All components used to manufacture the device are FDA approved materials. The pharmaceutical or other active agent may be included in either layer, but is preferably incorporated in the adhesive layer. This layer is in direct contact with the treatment site and the active compound will be released at a rate related to the dissolution of the adhesive layer. The backing layer will control the rate at which the adhesive layer hydrates, therefore control the rate of dissolution of the adhesive layer.

The adhesive layer may comprise at least one film-forming water-soluble polymer, typically selected from a family of cellulose polymers (the "film-forming polymer") and at least one or more polymers known in the art for its bioadhesive property (the "bioadhesive polymer"). The film-forming polymer may comprise hydroxyethyl cellulose, hydroxypropyl cellulose, hydroxypropylmethyl cellulose, hydroxyethylmethyl cellulose, alone or in combination thereof. The molecular weight of the film-forming polymer is in the range of $10^2$ to $10^6$, and more preferably between $10^3$ to $10^5$. The film-forming polymer may be crosslinked and/or the adhesive layer plasticized to alter the dissolution characteristics. The bioadhesive polymer contained in the adhesive layer may comprise polyacrylic acid(PAA), which may or may not be partially crosslinked, sodium carboxymethyl cellulose(NaCMC), and polyvinylpyrrolidone(PVP), alone or in combination thereof. These bioadhesive polymers are preferred because they exhibit good instantaneous mucoadhesive properties in the dry, film state. In the case of sodium carboxymethyl cellulose, typical average molecular weights range between 50,000 and 700,000 Daltons, and preferably between 60,000 and 500,000 Daltons, with a degree of substitution of 0.7. The substitution range varies between 0.5 and 1.5, and preferably between 0.6 and 0.9. The polyvinyl pyrrolidone can be characterized according to its average molecular weight and comprises between 5,000 and 150,000 Daltons, preferably between 10,000 and 100,000 Daltons. In some instances, the combination of some grades of polyvinyl pyrrolidone with polyacrylic acid may result in precipitation, causing a non-homogeneous adhesive layer to result and a potentially less than optimum mucoadhesive property. Such combinations of polyacrylic acid and polyvinyl pyrrolidone should be avoided. Other mucoadhesive polymers or combination of mucoadhesive polymers known in the art may also be used.

The chemical nature of the bioadhesive polymers used in the present invention, including chain, side groups and crosslinking agents, generates interactions between the mucosal constituents and the polymer or polymers, such as physical entanglement, Van der Waals forces, and hydrogen bonding. Since the mucosal surface differs from one individual to another and changes naturally over time, the use of a combination of at least two bioadhesive polymers and/or the use of a combination of different grades of the same polymer will provide maximum adhesion of the device for a wide range of different mucosal surfaces. However, the use of a single mucoadhesive polymer is effective as well. The ratio of bioadhesive polymer to film-forming polymer in the adhesive layer can be varied and depends upon the type and amount of pharmaceutical or other active ingredient used and other factors. However, the content of combined components in the adhesive layer is between 5 and 95% by weight, preferably between 10 and 80% by weight. In terms of weight percent of the different bioadhesive polymers PAA, NaCMC, and PVP, some examples are detailed later. Preferred combinations include PAA and NaCMC, NaCMC and PVP, or PAA and PVP, and also include the use of different molecular weight grades of the same polymer.

The non-adhesive backing layer is a precast film comprised of a water-soluble, film-forming pharmaceutically acceptable polymer such as hydroxyethyl cellulose, hydroxypropyl cellulose, hydroxyethylmethyl cellulose, hydroxypropylmethyl cellulose, polyvinyl alcohol, polyethylene glycol, polyethylene oxide, ethylene oxide-propylene oxide co-polymers, or other water soluble film-forming polymers, alone or in combination thereof. The non-adhesive backing layer is further modified to render it water erodible instead of water soluble. This is accomplished by coating the backing layer film with a more hydrophobic polymer selected from a group of FDA approved Eudragit polymers, ethyl cellulose and methyl cellulose polymers that are approved for use in other pharmaceutical dosage forms. Other hydrophobic polymers may be used, alone or in combination with other hydrophobic or hydrophilic polymers, provided that the layer derived from these polymers or combination of polymers erodes in a moist environment. The application of an erodible layer allows the backing layer to act as the support layer on which the adhesive solution can be cast without dissolution of the backing layer during the manufacture of the layered device of the present invention. The elimination of polyethylene or other rigid, non-erodible non-porous surface results, and therefore the device no longer represents a potential threat of user injury and can be manufactured on a cost effective and reproducible basis.

The type of solution used to coat the precast backing layer typically is composed of a mixture of a hydrophobic Eudragit polymer or copolymer, or ethyl or methyl cellulose, and a water soluble polymer such as polyvinyl pyrrolidone, hydroxypropyl methyl cellulose, hydroxyethyl cellulose, hydroxypropyl cellulose, polyvinyl alcohol or any other water soluble polymer that can be completely comixed with Eudragit or ethyl cellulose, dissolved in Ethanol or other suitable volatile organic solvent. The ratio of hydrophobic Eudragit or ethyl cellulose to water soluble polymer ranges from 0.5 to 18:1, and more preferably 1:0 to 10:1. The coating solution may also contain a plasticizing agent, such as propylene glycol, polyethylene glycol, or glycerine in a small amount, 0 to 2% by weight, in order to improve the "flexibility" of this layer in the mouth and to adjust the erosion rate of the device. In addition, humectants such as hyaluronic acid, glycolic acid, and other alpha hydroxyl acids can also be added to improve the "softness" and "feel" of the device. Finally, colors and opacifiers may be added to help distinguish the resulting non-adhesive backing layer from the mucoadhesive layer. Some opacifers include titanium dioxide, zinc oxide, zirconium silicate, etc.

The amount of mixed coating applied to the backing layer, using a suitable doctor blade or lab coater apparatus, ranges between zero and 1.5 mm, most preferably between 0.05 and 0.4 mm. The amount of solids present in the coating solution, the resulting solution viscosity and coating thickness applied determine the amount of coating film to be deposited on the precast backing layer. Typically, increasing the hydrophobic polymer to water soluble polymer ratio will provide a device with a longer residence time, while keeping coating thickness, viscosity, coating solids, polymer composition, and other variables constant. In addition, increasing the coating thickness of the Eugragit and/or ethyl cellulose/water-soluble polymer mixture while keeping all other variables constant will also provide an increased residence time. This will be clearly shown in examples shown later in this disclosure.

The residence time of the device of the present invention is dependent upon the composition of the modified backing layer and the rate of dissolution of the water-soluble polymers used. The residence time is easily controlled, from minutes to hours, by the amount of coating solution applied to the backing layer and the specific composition of the coating solution. The device of the present invention is therefore more versatile than those films, tablets and gels known in the art and can be used with a wider range of pharmaceuticals or other active compounds requiring different therapeutic delivery times. The device of the present invention also typically provides, when desired, a longer residence time than those devices known in the art. This is a result of the selection of the appropriate backing layer formulation, providing a slower rate of erosion of the backing layer and therefore allowing the mucoadhesive layer to remain in contact with the treatment site for a longer period of time before complete erosion. The device of the present invention will maximize the unidirectional delivery of an active compound to the treatment site while minimizing the systemic delivery of the drug that results from surface erosion due to saliva or other bodily fluids. The device of the present invention is more therapeutically effective for most indications than those devices known in the art, since a sustained level of drug is delivered at a more controlled rate over a longer treatment time.

The pharmaceutical agent or other active compound of the present invention may comprise a single pharmaceutical or a combination of pharmaceuticals. These active ingredients may be incorporated in the adhesive layer, backing layer or in both. If desired, flavoring agents known in the art may be added to mask the taste of the active compound. Penetration enhancers may also be included in the adhesive layer to help reduce the resistance of the mucosa to drug transport. Typical enhancers known in the art include ethylenediamine tetracetic acid, chitosans, dimethyl sulfoxide, etc. Ingredients to enhance drug solubility and/or stability of the drug may also be added to the layer or layers containing the active ingredient. Examples of stabilizing and solubilizing agents are cyclodextrins.

Pharmaceuticals that may be used, either alone or in combination, include antiallergic compounds, antianginal agents, anti-inflammatory analgesic agents, steroidal anti-inflammatory agents, antihistamines, local anesthetics, bactericides and disinfectants, vasoconstrictors, hemostatics, chemotherapeutics, antibiotics, keratolytics, cauterizing agents, hormones, growth hormones and growth hormone inhibitors, analgesic narcotics, and antiviral drugs.

Examples of antiallergic compounds include amlexanox, astemizole, azelastinep, emirolast, alopatadine, cromolyn, fenpiprane, repirinast, tranilast, and traxanox.

Examples of antianginal agents include nifedipine, atenolol, bepridil, carazolol, and epanolol.

Examples of anti-inflammatory analgesic agents include acetaminophen, methyls alicylate, monoglycol salicylate, aspirin, mefenamic acid, flufenamic acid, indomethacin, diclofenac, alclofenac, diclofenac sodium, ibuprofen, ketoprofen, naproxen, pranoprofen, fenoprofen, sulindac, fenclofenac, clidanac, flurbiprofen, fentiazac, bufexamac, piroxicam, phenylbutazone, oxyphenbutazone, clofezone, pentazocine, mepirizole, tiaramide hydrochloride, etc.

Examples of steroidal anti-inflammatory agents include hydrocortisone, predonisolone, dexamethasone, triamcinolone acetonide, fluocinolone acetonide, hydrocortisone acetate, predonisolone acetate, methylpredonisolone, dexamethasone acetate, betamethasone, betamethasone valerate, flumetasone, fluorometholone, beclomethasone diproprionate, etc.

Examples of antihistamines include diphenhydramine hydrochloride, diphenhydramine salicylate, diphenhydramine, chlorpheniramine hydrochloride, chlorpheniramine maleate isothipendyl hydrochloride, tripelennamine hydrochloride, promethazine hydrochloride, methdilazine hydrochloride, etc.

Examples of local anesthetics include dibucaine hydrochloride, dibucaine, lidocaine hydrochloride, lidocaine, benzocaine, p-buthylaminobenzoic acid 2-(diethylamino) ethyl ester hydrochloride, procaine hydrochloride, tetracaine, tetracaine hydrochloride, chloroprocaine hydrochloride, oxyprocaine hydrochloride, mepivacaine, cocaine hydrochloride, piperocaine hydrochloride, dyclonine, dyclonine hydrochloride, etc.

Examples of bactericides and disinfectants include thimerosal, phenol, thymol, benzalkonium chloride, benzethonium chloride, chlorhexidine, povidone iodine, cetylpyridinium chloride, eugenol, trimethylammonium bromide, benzoic acid, sodium benzoate, etc.

Examples of vasoconstrictors include naphazoline nitrate, tetrahydrozoline hydrochloride, oxymetazoline hydrochloride, phenylephrine hydrochloride, tramazoline hydrochloride, etc.

Examples of hemostatics include thrombin, phytonadione, protamine sulfate, aminocaproic acid, tranexamic acid, carbazochrome, carbaxochrome sodium sulfanate, rutin, hesperidin, etc.

Examples of chemotherapeutic drugs include sulfamine, sulfathiazole, sulfadiazine, homosulfamine, sulfisoxazole, sulfisomidine, sulfamethizole, nitro furazone, taxanes, platinum compounds, topoisomerase I inhibitors, and anthrocycline.

Examples of antibiotics include penicillin, meticillin, oxacillin, cefalotin, cefalordin, erythromycin, lincomycin, tetracycline, chlortetracycline, oxytetracycline, metacycline, chloramphenicol, kanamycin, streptomycin, gentamicin, bacitracin, cycloserine, and clindamycin.

Examples of keratolytics include salicylic acid, podophyllum resin, podolifox, and cantharidin.

Examples of cauterizing agents include the chloroacetic acids and silver nitrate.

Examples of hormones include estrone, estradiol, testosterone, equilin, and human growth hormone.

Examples of growth hormone inhibitors are octreotide and somatostatin.

Examples of analgesic narcotics include fentanyl, buprenorphine, codeine sulfate, levorphanol, and morphine hydrochloride.

Examples of antiviral drugs include protease inhibitors, thymidine kinase inhibitors, sugar or glycoprotein synthesis inhibitors, structural protein synthesis inhibitors, attachment and adsorption inhibitors, and nucleoside analogues such as acyclovir, penciclovir, valacyclovir, and ganciclovir.

The amount of active agent or pharmaceutical(s) in the device of the present invention depends upon the therapeutic requirements, although, preferably, the pharmaceutical component comprises 0.001 to 30% by weight of the device, and more preferably between 0.005 and 20% by weight.

Flavoring agents, preservatives, plasticizers, opacifiers, stabilizing and solubilizing compounds, penetration enhancers and coloring agents may also be included in the adhesive layer, backing layer, or both layers of the device. Preferably, these components represent no more than 5% by weight of the final device.

The thickness of the device may vary, depending upon the thickness of each individual layer. Preferably, the thickness of the layered disc of the present invention ranges from 0.05 mm to 1 mm, and more preferably from 0.1 to 0.5 mm. The thickness of each individual layer may vary from 10 to 90% of the overall thickness of the layered device, and preferably varies from 30 to 60%. Therefore, the preferred thickness of each layer may vary from 0.002 mm to 0.9 mm, and more preferably from 0.003 to 0.6 mm.

The pharmaceutical delivery device of the present invention may be prepared by various methods known in the art. In one embodiment, the components are dissolved in the appropriate solvent or combination of solvents to prepare a solution. Solvents for use in the present invention may comprise water, methanol, ethanol, isopropyl alcohol, acetone, methyl ethyl ketone, heptane, or dichloroethane, alone or in combination. The residual solvent content in the dried, multilayered film may act as a plasticizer, an erosion-rate-modifying agent or may provide some pharmaceutical benefit. Desired residual solvent may reside in either or both layers.

Each solution is then coated onto the precast backing layer that acts as the substrate or support layer. Eventually, one of the components might be in suspension. While it is desirable for all components in each coating solution to be in solution, coating solutions in which one or more components are partially or fully suspended in the coating solution may also be used. Each solution is cast and processed into a thin film by techniques known in the art, such as by film dipping, film coating, film casting, spin coating, or spray drying. The thin film is then dried. This drying process may be accomplished using any suitable type of oven. However, the solvent residuals are dependent upon the drying procedure and parameters used. Alternatively, the individual layers of the multi-layered device can be produced independently and then laminated together or may be filmed one on top of the other. In one embodiment of the present invention, a precast film used as the backing and support layer is coated first with an alcoholic polymeric solution containing the appropriate mixture of hydrophobic and water soluble polymers. After subsequent drying, the coated precast backing layer is then top-coated or coated on the reverse side with the appropriate mucoadhesive solution that may or may not contain a pharmaceutical or other active agent. After appropriate drying, the multilayered film obtained may be cut into any size or shape, for application to the mucosal tissue. Some possible shapes include disks, ellipses, squares, rectangles, and parallelepipeds.

Methods for treating mucosal surfaces, specifically oral mucosa, surrounding tissues, and bodily fluids for localized and systemic drug delivery are provided. In one embodiment, the method comprises applying a multi-layered, adherent film to the treatment site in order to provide drug delivery and protection to the underlying site. The adherent film may comprise any of the layered devices provided herein. In a preferred embodiment, the method comprises application of a multi-layered pharmaceutical carrier device having a first mucoadhesive layer, a second backing layer that also acts as a support layer and a third layer that regulates the residence time of the device. The pharmaceutical or other active compound may be present in the adhesive layer, backing layer, or both layers.

EXAMPLE 1

A 300 gram batch of mucoadhesive coating solution was prepared using 268.2 grams of deionized and 0.22@ filtered water, 5.40 grams of hydroxyethyl cellulose, Natrosol 250 L NF (B F Goodrich), 3.19 grams Amlexanox, 2-amino-7-isopropyl-5-oxo-5H-{1} benzopyranol {2,3-b}-pyridine-3-carboxylic acid (Takeda Chemical Industries), 7.81 grams Noveon AA1, Polycarbophil (B F Goodrich), 13.50 grams sodium carboxymethyl cellulose, 7LF PH (B F Goodrich), 0.96 grams sodium benzoate, NF(Spectrum Chemicals), and 0.95 grams propylene glycol, USP(Spectrum Chemicals). A Lighnin® mixer with an A-100 propeller was used to effectively homogenize this viscous mucoadhesive coating suspension at a speed of 1000 rpm. The resulting percentage of film forming polymer was 1.8% and the mucoadhesive polymers was 7.1%. This adhesive coating suspension was used in some of the examples shown below.

EXAMPLE 2

A 500 gram batch of mucoadhesive coating solution was prepared using 451.5 grams of deionized and 0.22 micron filtered water, 8.0 grams of hydroxyethyl cellulose, Natrosol 250 L NF (B F Goodrich ), 9.0 grams Amlexanox, 2-amino-7-isopropyl-5-oxo-5H-{1} benzopyranol {2,3-b}-pyridine-3-carboxylic acid (Takeda Chemical Industries), 11.0 grams Noveon AA1, Polycarbophil (B F Goodrich), 17.0 grams sodium carboxymethyl cellulose, 7LF PH (B F Goodrich), 1.0 grams of hydroxypropyl cellulose, Klucel EF Pharm (B F Goodrich), 1.5 grams sodium benzoate, NF(Spectrum Chemicals), and 1.0 grams propylene glycol, USP (Spectrum Chemicals). A Lighnin® mixer with an A-100 propeller was used to effectively homogenize this viscous mucoadhesive coating suspension at a speed of 1000 rpm. The resulting percentage of film forming polymer was 1.8% and the mucoadhesive polymers was 5.6%. This adhesive coating suspension was used in some of the examples to follow.

EXAMPLE 3

In order to prepare a variety of hydrophobic coating solutions to be used to produce multilayered films of different residence times, stock solutions of both polyvinylpyrrolidone (pvp), 16% w/w of PVP, USP, one million molecular weight (BASF), dissolved in ethanol, USP, 190 proof (Spectrum Chemicals), and ethyl cellulose, 20% w/w of ethyl cellulose dissolved in ethanol, USP, 190 proof were prepared. Aliquots of both stock solutions were combined using a Lightning mixer to create a range of coating solutions as follows:

3a. twenty grams of pvp solution plus 16 grams of ethyl cellulose solution produced a mixed coating solution ratio of 1:1 (ethyl cellulose: pvp)

3b. twenty grams of pvp solution plus 20 grams of ethyl cellulose solution produced a mixed coating solution ratio of 1.25:1 (ethyl cellulose:pvp)

3c. twenty grams of pvp solution plus 28 grams of ethyl cellulose solution produced a mixed coating solution ratio of 1.75:1 (ethyl cellulose;pvp)

3d. twenty grams of pvp solution plus 32 grams of ethyl cellulose solution produced a mixed coating solution ratio of 2:1 (ethyl cellulose:pvp)

3e. twenty grams of pvp solution plus 40 grams of ethyl cellulose solution produced a mixed coating solution ratio of 2.5:1 (ethyl cellulose:pvp)

EXAMPLE 4

Similar to example 3, additional hydrophobic coating solutions were prepared using stock solutions of both polyvinylpyrrolidone, 16% w/w of PVP, USP, one million molecular weight(BASF), dissolved in ethanol, USP, 190 proof(Spectrum Chemicals), and Eudragit® RS-100 NF(quaternary ammonium acrylate/methacrylate co-polymers) (Rohm GmbH), 48% w/w of polymer dissolved in ethanol, USP, 190 proof. Aliquots of both stock solutions were combined using a lightning mixer to create a range of coating solutions as follows:

4a. twenty grams of pvp solution plus 6.67 grams of Eudragit® solution produced a mixed coating solution ratio of 1:1 (Eudragit®: pvp)

4b. twenty grams of pvp solution plus 13.34 grams of Eudragit® solution produced a mixed coating solution ratio of 2:1 (Eudragit®: pvp)

4c. twenty grams of pvp solution plus 23.33 grams of Eudragit® solution produced a mixed coating solution ratio of 3.5:1 (Eudragit®: pvp )

4d. twenty grams of pvp solution plus 26.67 grams of Eudragit® solution produced a mixed coating solution ratio of 4:1 (Eudragit®: pvp)

4e. twenty grams of pvp solution plus 40.0 grams of Eudragit® solution produced a mixed coating solution ratio of 6:1 (Eudragit®: pvp )

4f. twenty grams of pvp solution plus 60.0 grams of Eudragit® solution produced a mixed coating solution ratio of 9:1 (Eudragit®: pvp)

EXAMPLE 5

Multi-layered films were prepared using the hydrophobic coatings solutions outlined in example 3 with the mucoadhesive coating suspension detailed in example 1. First, a piece of hydroxypropyl methyl cellulose precast film (Watson Polymer Films), 0.004 inches thick was cut approximately 18 inches×11.5 inches and placed in the paper and foil holder of a Werner Mathis AG Lab Coater, type LTF. The doctor blade setting was adjusted to 0.15 mm. and each solution from example 3 was applied to individual precast pieces of the backing film. The films were then automatically dried in the oven portion of the lab coater, and a smooth, integral layer of deposited hydrophobic/water soluble polymer resulted. Each coated film was removed and put back into the frame with the uncoated side of the backing layer facing up. The adhesive coating suspension from example 1. was then used to coat each of the coated backing layer samples, using a 1.2 mm. setting on the doctor blade. The films were dried as before, and a second coating and drying step using the adhesive layer was conducted. These multilayered films were kept in a water impermeable plastic bag prior to being used for in-vivo testing. Samples were designated as 5.3a, 5.3b, 5.3c, 5.3d, and 5.3e. For example, sample 5.3c refers to a multilayered film composed of a backing layer of hydroxypropyl methyl cellulose coated with a film composed of a mixture of ethyl cellulose and polyvinyl pyrrolidone at a ratio of 1.75:1 and a mucoadhesive layer from example 1., using a coating setting for the hydrophobic coating solution at 0.15 mm.

EXAMPLE 6

The experimental process outlined in example 5 was repeated exactly, with the exception that the coating setting for the hydrophobic/water soluble coating process was 0.25 mm instead of 0.15 mm. The effect of increasing the amount of coating thickness and the resulting residence time will be shown and tabulated in later examples. Samples were designated similarly as in example 5. For example, sample 6.3b is the same compositionally as sample 5.3b, except the 6.3b sample contains a thicker ethyl cellulose/pvp coating.

EXAMPLE 7

Multi-layered films were prepared using the Eudragit®/pvp coatings solutions outlined in example 4 with the mucoadhesive coating suspension detailed in example 2. First, a piece of hydroxypropyl methyl cellulose precast film(Watson Polymer Films), 0.004 inches thick was cut approximately 18 inches×11.5 inches and placed in the paper and foil holder of a Werner Mathis AG Lab Coater, type LTF. The doctor blade setting was adjusted to 0.25 mm. and each solution from example 4 was applied to individual precast pieces of the backing film. The films were then automatically dried in the oven portion of the lab coater, and a smooth, integral layer of deposited hydrophobic/water soluble polymer resulted. Each coated film was removed and put back into the frame with the uncoated side of the backing layer facing up. The mucoadhesive coating suspension from example 2 was then used to coat each of the coated backing layer samples, using a 1.2 mm. setting on the doctor blade. The films were dried as before, and a second coating and drying step using the adhesive layer was conducted. These multilayered films were kept in a water impermeable plastic bag prior to being used for in-vivo testing. Samples were designated as 7.4a, 7.4b, 7.4c, 7.4d, 7.4e and 7.4f. For example, sample 7.4c refers to a multilayered film composed of a backing layer of hydroxypropyl methyl cellulose coated with a film composed of a mixture of Eudragit® and polyvinyl pyrrolidone at a ratio of 3.5:1 and a mucoadhesive layer from example 2. using a doctor blade setting for the hydrophobic coating solution at 0.25 mm.

EXAMPLE 8

The experimental process outlined in example 7 was repeated exactly, with the exception that the doctor blade setting for the hydrophobic/water soluble coating process was 0.5 mm instead of 0.25 mm. The effect of increasing the amount of coating thickness and the resulting residence time will be shown and tabulated in later examples. Samples were designated similarly as in example 7. For example, 8.4b is the same compositionally as sample 7.4b, except the 8.4b sample contains a thicker Eudragit®/pvp coating.

EXAMPLE 9

Using the stock solutions detailed in example 3, 5.0 grams of pvp solution plus 7.0 grams of ethyl cellulose solution were mixed. To this solution, 0.7 grams of green food color(Kroger Company), 2% dye(yellow 5 and blue 1) in propylene glycol/water was added and thoroughly mixed. A piece of hydroxypropyl methyl cellulose precast film (Watson Polymer Films), 0.004 inches thick was cut approximately 18 inches×11.5 inches and placed in the paper and foil holder of a Werner Mathis AG Lab Coater, type LTF. The doctor blade setting was adjusted to 0.15 mm. and the solution was coated and dried on the precast backing layer. A smooth, green colored, uniform coating resulted.

The film was removed and reversed in the holder, and coated and dried similarly as detailed in example 5 using the mucoadhesive coating suspension shown in example 1. The resulting layered film exhibited a good contrast in color, a green outer layer that provides an appropriate residence time and the white, opaque mucoadhesive layer that is meant to be applied to the oral mucosa. Thus, the inclusion of an innocuous FDA approved dye provides a visual aid to the end user for the proper orientation of the mucoadhesive layer onto the treatment site.

EXAMPLE 10

To ascertain the in-vivo performance of the multilayered drug delivery devices, films from the preceeding examples were cut into 0.5 inch disks using a die punch. The mucoadhesive layer was carefully oriented onto the oral, mucosal cheek surface using an index finger and applying continuous pressure to maximize initial adhesion for two to four seconds. Parameters such as initial tack, comfort, and residence time were recorded. These results are tabulated as follows:

| Sample # | Initial Tack | Comfort | Residence Time |
| --- | --- | --- | --- |
| 5.3a | Ok | Good | 51 min |
| 5.3b | Ok | Good | 75 min |
| 5.3c | Ok | good | 79 min |
| 5.3d | Ok | good | 99 min |
| 5.3e | Ok | good | 125 min |
| 6.3a | Ok | good | 68 min |
| 6.3b | Ok | good | 94 min |
| 6.3c | Ok | good | 131 min |
| 6.3d | — | — | — |
| 6.3e | — | — | — |
| 7.4a | Ok | good | 40 min |
| 7.4b | — | — | — |
| 7.4c | — | — | — |
| 7.4d | Ok | ok | 115 min |
| 7.4e | Ok | ok | 120 min |
| 7.4f | Ok | ok | >120 min |
| 8.4a | Ok | good | 50 min |
| 8.4b | Ok | good | 65 min |

-continued

| Sample # | Initial Tack | Comfort | Residence Time |
|---|---|---|---|
| 8.4c | Ok | good | 100 min |
| 8.4d | Ok | ok | 165 min |
| 8.4e | Ok | ok | 180 min |
| 8.4f | Ok | ok | >240 min |
| 9 | Ok | good | 158 min |

It is clear from the above table that longer residence times for these multilayered pharmaceutical drug delivery devices are provided using coating solutions that contain higher amounts of hydrophobic polymer relative to the water-soluble polymer present. In addition, by increasing the amount of coating thickness, a concomitant increase in residence time results.

It is also apparent that using ethyl cellulose instead of Eugdragit® as the hydrophobic polymer component in the coating solution provides a longer residence time at the same relative concentration to the water soluble polyvinylpyrrolidone component. In all likelihood, this is a result of the greater hydrophobicity of ethyl cellulose. One other conclusion is that the presence of a food dye and propylene glycol in the hydrophobic coating solution also provided an increase in residence time, about double what was expected. Our hypothesis is that the dye and/or propylene glycol plasticize the hydrophobic coating matrix, causing a slower erosion process to occur and therefore increasing the residence time. This finding also allows the user to potentially modify the residence time by changes in propylene glycol and dye concentration in the final hydrophobic coating layer of the multilayered film device.

The U.S. patents and any other references cited above are incorporated in pertinent part by reference herein for the reasons cited.

Those skilled in the art will recognize that, while specific embodiments and examples have been described, various modifications and changes may be made without departing from the scope and spirit of this invention.

What is claimed is:

1. A mucoadhesive, erodible multi-layered device comprising a first, water-soluble adhesive layer to be placed in contact with a mucosal surface and a second, water-erodible non-adhesive backing layer that controls residence time of the device;
   wherein said first layer comprises at least one water-soluble film-forming polymer in combination with at least one mucoadhesive polymer; and said second, water-erodible non-adhesive backing layer comprises a precast film containing at least one of hydroxypropyl methylcellulose, hydroxyethyl cellulose, hydroxypropyl cellulose, polyvinyl alcohol, polyethylene glycol, polyethylene oxide, and ethylene oxide-propylene oxide co-polymer, said backing layer being coated with at least one hydrophobic polymer, alone or in combination with at least one hydrophilic polymer, such that the backing layer is bioerodible.

2. The device of claim 1 defined further as for use with or without an incorporated pharmaceutical agent.

3. The device of claim 1 defined further as being for protection of a mucosal site or the administration of a pharmaceutical agent locally, regionally or systemically.

4. The mucoadhesive, erodible multi-layered device of claim 1, wherein said first water-soluble adhesive layer comprises at least one water-soluble film-forming polymer selected from the group consisting of hydroxyethyl cellulose, hydroxypropyl cellulose, hydroxypropyl methylcellulose, and hydroxyethyl methylcellulose, in combination with at least one mucoadhesive polymer selected from the group consisting of polyacrylic acid, polyvinyl pyrrolidone, and sodium carboxymethyl cellulose.

5. The mucoadhesive, erodible multi-layered device of claim 1, wherein said second water-erodible non-adhesive backing layer acts as a casting and support surface on which the adhesive layer is prepared, and comprises a premade film of hydroxypropyl methyl cellulose in combination with a coating consisting of at least one hydrophobic polymer selected from the family of quaternary ammonium acrylate/methacrylate co-polymers, (Eudragit RS) ethyl cellulose and methyl cellulose, alone or in combination with at least one hydrophilic polymer, selected from the group consisting of polyvinyl pyrrolidone, hydroxypropyl methylcellulose, hydroxyethyl cellulose, hydroxypropyl cellulose, and polyvinyl alcohol.

6. The mucoadhesive, erodible multi-layered device of claim 1, wherein said second water-erodible non-adhesive backing layer comprises a premade film of hydroxypropyl methylcellulose and a coating of a hydrophobic and hydrophilic polymer mixture at a ratio of 0.5:1 to 18:1.

7. The device of claim 1 wherein said second water-erodible non-adhesive backing layer comprises a premade film of hydroxypropyl methylcellulose and a coating of a hydrophobic and hydrophilic polymer mixture at a ratio of 1:0 to 10:1.

8. The device of claim 6 where the non-adhesive backing layer comprises a precast film of hydroxypropyl methylcellulose and coating mixture of hydrophobic and hydrophilic polymers at a ratio of 1:0 to 10:1, wherein the coating contains at least one of propylene glycol, polyethylene glycol, or glycerine, as a plasticizer to improve flexibility.

9. The device of claim 6 where the non-adhesive backing layer comprises a premade film of hydroxypropyl methylcellulose and coating mixture of hydrophobic and hydrophilic polymers at a ratio of 1:0 to 10:1, wherein the coating mixture contains at least one of hyaluronic acid and alpha hydroxyl acid as a humectant to improve softness or feel.

10. The device of claim 9 where the humectant is glycolic acid.

11. The device of claim 1 where the non-adhesive backing layer comprises a precast film of hydroxypropyl methylcellulose and coating mixture of hydrophobic and hydrophilic polymers at a ratio of 1:0 to 10:1, wherein the coating mixture contains titanium dioxide, zinc oxide, or zirconium silicate as an opacifier one or less FD&C Red, Yellow, Green or Blue as a coloring agent to help distinguish the backing layer from the mucoadhesive layer.

12. The mucoadhesive, erodible multi-layered device of claim 1 wherein said backing layer comprises a premade film of hydroxypropyl methyl cellulose, a coating comprising a mixture of hydrophobic and hydrophilic polymers at a ratio of 1:0 to 10:1, a plasticizer, and a coloring agent or an opacifier whose combined total is less than about 4% by weight of the device.

13. The mucoadhesive, erodible multi-layered device of claim 1 further comprising at least one pharmaceutical agent incorporated within said first or second layer.

14. The multi-layered pharmaceutical carrier device of claim 13, wherein said first or second layer contains a flavoring agent to mask the taste of the pharmaceutical agent or to improve patient compliance.

15. The multi-layered pharmaceutical carrier device of claim 13, wherein said pharmaceutical agent comprises an anti-allergic agent.

16. The multi-layered pharmaceutical carrier device of claim 15, wherein said anti-allergic agent is amlexanox, astemizole, azelastinep, emirolast, alopatadine, cromolyn, fenpiprane, repirinast, tranilast, or traxanox.

17. The multi-layered pharmaceutical carrier device of claim 13, wherein said pharmaceutical agent comprises an anti-inflammatory analgesic agent.

18. The multi-layered pharmaceutical carrier device of claim 17, wherein said anti-inflammatory analgesic agent is acetaminophen, methyl salicylate, monoglycol salicylate, aspirin, mefenamic acid, flufenamic acid, indomethacin, diclofenac, alclofenac, diclofenac sodium, ibuprofen, ketoprofen, naproxen, pranoprofen, fenoprofen, sulindac, fenclofenac, clidanac, flubiprofen, fentiazac, bufexamac, piroxicam, phenylbutazone, oxyphenbutazone, clofezone, pentazocine, mepirizole, or tiaramide hydrochloride.

19. The multi-layered pharmaceutical carrier device of claim 13, wherein said pharmaceutical agent comprises an antianginal agent.

20. The multi-layered pharmaceutical carrier device of claim 19, wherein said antianginal agent is nifedipine, atenolol, bepridil, carazolol, or epanolol.

21. The multi-layered pharmaceutical carrier device of claim 13, wherein said pharmaceutical agent comprises a steroidal anti-inflammatory agent.

22. The multi-layered pharmaceutical carrier device of claim 21, wherein said steroidal anti-inflammatory agent is hydrocortisone, predonisolone, dexamethasone, triamcinolone acetonide, fluocinolone acetonide, hydrocortisone acetate, predonisolone acetate, methylpredonisolone, dexamethasone acetate, betamethasone, betamethasone valerate, flutetasone, fluormetholone, or orbeclomethasone dipropionate.

23. The multi-layered pharmaceutical carrier device of claim 13, wherein said pharmaceutical agent comprises an antihistamine.

24. The multi-layered pharmaceutical carrier device of claim 23, wherein said antihistamine is diphenhydramine hydrochloride, chlorpheniramine maleate, isothipendyl hydrochloride, tripelennamine hydrochloride, promethazine hydrochloride, or methdilazine hydrochloride.

25. The multi-layered pharmaceutical carrier device of claim 13, wherein said pharmaceutical agent comprises a local anesthetic.

26. The multi-layered pharmaceutical carrier device of claim 25, wherein said local anesthetic is dibucaine hydrochloride, dibucaine, lidocaine hydrochloride, lidocaine, benzocaine, p-buthylaminobenzoic acid, 2-(diethylamino) ethyl ester hydrochloride, procaine hydrochloride, tetracaine, tetracaine hydrochloride, chloroprocaine hydrochloride, oxyprocaine hydrochloride, mepivacaine, cocaine hydrochloride, piperocaine hydrochloride, dyclonine, or dyclonine hydrochloride.

27. The multi-layered pharmaceutical carrier device of claim 13, wherein said pharmaceutical agent comprises a bactericide or disinfectant.

28. The multi-layered pharmaceutical carrier of claim 27, wherein said bactericide or disinfectant is thimerosal, phenol, thymol, benzalkonium chloride, chlorhexidine, povidone iodine, cetylpyridinium chloride, eugenol, trimethylammonium bromide, benzoic acid or sodium benzoate.

29. The multi-layered pharmaceutical carrier device of claim 13, wherein said pharmaceutical agent comprises a vasoconstrictor.

30. The multi-layered pharmaceutical carrier device of claim 29, wherein said vasoconstrictor is naphazoline nitrate, tetrahydrozoline hydrochloride, oxymetazoline hydrochloride, phenylephrine hydrochloride, or tramazolinehydrochloride.

31. The multi-layered pharmaceutical carrier device of claim 13, wherein said pharmaceutical agent comprises a hemostatic agent.

32. The multi-layered pharmaceutical carrier device of claim 31, wherein said hemostatic agent is thrombin, phytonadione, protamine sulfate, aminocaproic acid, tranexamic acid, carbazochrome, carbaxochrome sodium sulfate, rutin, or hesperidin.

33. The multi-layered pharmaceutical carrier device of claim 13, wherein said pharmaceutical agent comprises a chemotherapeutic agent.

34. The multi-layered pharmaceutical device of claim 33, wherein said chemotherapeutic agent is sulfamine, sulfathiazole, sulfadiazine, homosulfamine, sulfisoxazole, sulfisomidine, sulfamethizole, nitrofurazone, taxanes, platinum compound, topoisomerase 1 inhibitor, or anthracycline.

35. The multi-layered pharmaceutical carrier device of claim 13, wherein said pharmaceutical agent comprises an antibiotic.

36. The multi-layered pharmaceutical carrier device of claim 35, wherein said antibiotic is penicillin, meticillin, oxacillin, cefalotin, cefalordin, erythromycin, lincomycin, tetracycline, chlortetracycline, oxytetracycline, chloramphenicol, kanamycin, streptomycin, gentamicin, bacitracin, cycloserine, or clindamycin.

37. The multi-layered pharmaceutical carrier device of claim 13, wherein said pharmaceutical agent comprises a keratolytic agent.

38. The multi-layered pharmaceutical carrier device of claim 37, wherein said keratolytic agent is salicylic acid, podophyllum resin, podolifox, or cantharidin.

39. The multi-layered pharmaceutical carrier device of claim 13, wherein said pharmaceutical agent comprises a cauterizing agent.

40. The multi-layered pharmaceutical carrier device of claim 39, wherein said cauterizing agent is chloroacetic acid or silver nitrate.

41. The multi-layered pharmaceutical carrier device of claim 13, wherein said pharmaceutical agent comprises a hormone.

42. The multi-layered pharmaceutical carrier device of claim 41, wherein said hormone is estrone, estradiol, testosterone, equilin, or human growth hormone.

43. The multi-layered pharmaceutical carrier device of claim 13, wherein said pharmaceutical agent comprises a growth hormone inhibitor.

44. The multi-layered pharmaceutical carrier device of claim 43, wherein said growth hormone inhibitor is octreotide or somatostatin.

45. The multi-layered pharmaceutical carrier device of claim 13, wherein said pharmaceutical agent comprises an analgesic narcotic.

46. The multi-layered pharmaceutical carrier device of claim 45, wherein said analgesic narcotic is fentanyl, buprenorphine, codeine sulfate, levophanol, or morphine hydrochloride.

47. The multi-layered pharmaceutical carrier device of claim 13, wherein said pharmaceutical agent comprises an antiviral drug.

48. The multi-layered pharmaceutical carrier device of claim 47, wherein said antiviral drug is a protease inhibitor, thymidine kinase inhibitor, sugar or glycoprotein synthesis inhibitor, structural protein synthesis inhibitor, attachment and adsorption inhibitor, or nucleoside analogue.

49. The device of claim 48 where the analogue is acyclovir, penciclovir, valacyclovir, or ganciclovir.

50. The multi-layered pharmaceutical carrier device of claim 13, wherein the pharmaceutical agent comprises between about 0.001 and about 30 percent by weight of the device.

51. The multi-layered pharmaceutical carrier device of claim 13 wherein the pharmaceutical agent comprises between about 0.005 and about 20 percent by weight of the device.

* * * * *